(12) United States Patent
Buesseler et al.

(10) Patent No.: US 11,116,476 B2
(45) Date of Patent: Sep. 14, 2021

(54) ULTRASONIC TRANSDUCER ARRAY CATHETER WITH INTEGRATED COUPLER

(71) Applicant: St. Jude Medical, Cardiology Division, Inc., St. Paul, MN (US)

(72) Inventors: Ryan Kenneth Buesseler, Bristow, VA (US); Troy T. Tegg, Elk River, MN (US); Bruce Ebner, Shorewood, MN (US); Fermin A. Lupotti, Lake Forest, CA (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 465 days.

(21) Appl. No.: 15/948,818

(22) Filed: Apr. 9, 2018

(65) Prior Publication Data
US 2018/0289356 A1 Oct. 11, 2018

Related U.S. Application Data

(60) Provisional application No. 62/484,267, filed on Apr. 11, 2017.

(51) Int. Cl.
*A61B 8/12* (2006.01)
*A61B 8/00* (2006.01)
*A61M 25/01* (2006.01)

(52) U.S. Cl.
CPC .............. *A61B 8/4411* (2013.01); *A61B 8/12* (2013.01); *A61B 8/4254* (2013.01); *A61B 8/445* (2013.01); *A61M 25/0127* (2013.01); *A61M 25/0136* (2013.01); *A61M 25/0147* (2013.01)

(58) Field of Classification Search
CPC ....... A61B 8/12; A61B 8/4254; A61B 8/4411; A61B 8/445; A61M 25/0127; A61M 25/0136; A61M 25/0147
See application file for complete search history.

(56) References Cited

U.S. PATENT DOCUMENTS

| | | | |
|---|---|---|---|
| 6,254,573 B1 | 7/2001 | Haim et al. | |
| 6,709,396 B2 | 3/2004 | Flesch et al. | |
| 8,058,776 B1* | 11/2011 | Gibson | G01H 11/08 |
| | | | 310/336 |
| 2003/0113303 A1 | 6/2003 | Schwartz | |
| 2008/0009745 A1 | 1/2008 | Hossack | |
| 2010/0152590 A1 | 6/2010 | Moore | |
| 2015/0209007 A1 | 7/2015 | Garbini | |
| 2015/0272734 A1* | 10/2015 | Sheps | A61F 2/2445 |
| | | | 623/2.11 |
| 2017/0120080 A1* | 5/2017 | Phillips | A61N 7/022 |
| 2017/0319269 A1 | 11/2017 | Oliverius et al. | |

FOREIGN PATENT DOCUMENTS

| | | |
|---|---|---|
| WO | 2004021404 A2 | 3/2004 |
| WO | 2007115307 A2 | 10/2007 |
| WO | 2010117630 A | 10/2010 |

* cited by examiner

*Primary Examiner* — Mark D Remaly
(74) *Attorney, Agent, or Firm* — Dykema Gossett PLLC

(57) ABSTRACT

Aspects of the present disclosure are directed to an intravascular catheter with a coupler near a distal end which facilitates precise positioning of an end effector and one or more magnetic localization sensors.

18 Claims, 9 Drawing Sheets

ULTRASONIC TRANSDUCER ARRAY CATHETER WITH INTEGRATED COUPLER

CROSS REFERENCE TO RELATED APPLICATION

This application claims the benefit of U.S. Provisional Application No. 62/484,267, filed 11 Apr. 2017, the entire disclosure of which is incorporated herein by reference.

BACKGROUND a. Field

The instant disclosure relates to catheters including ultrasonic transducer arrays, and to methods of manufacturing intravascular catheters including ultrasonic transducer arrays. In some specific embodiments, the instant disclosure relates to intravascular catheters capable of ultrasound imaging and magnetic positioning.

BRIEF SUMMARY

Aspects of the present disclosure are directed to an intravascular catheter with a coupler, at a distal end of the catheter, which facilitates precise and efficient placement of an ultrasonic transducer array and one or more localization sensors during assembly and to maintain such placement during operation of the catheter.

Various aspects of the present disclosure are directed to methods of manufacturing an ultrasonic transducer array catheter. Some methods of manufacturing disclosed herein include utilizing a coupler at a distal end of an intravascular catheter to facilitate precise assembly of components therein. In some specific embodiments, the coupler may precisely control relative positioning of at least one of: steering components, an ultrasonic transducer array, magnetic localization sensors, and a temperature sensor.

Aspects of the present disclosure are directed to an intravascular catheter including an ultrasonic transducer array, a coupler mechanically coupled to a proximal end of the ultrasonic transducer array, a first and a second magnetic positioning sensor coupled to the coupler, a catheter shaft coupled to a proximal end of the coupler, and a catheter handle. The catheter handle is coupled to a proximal end of the catheter shaft, and steers the catheter through a vascular lumen of a patient. In more specific embodiments, the coupler is further configured to house and position the two magnetic positioning sensors at nonparallel orientations relative to one another, the two magnetic positioning sensors transmit electrical signals indicative of the six degrees of freedom that the ultrasonic transducer array has within a controlled magnetic field.

In some embodiments of the present disclosure, a coupler assembly for an intravascular catheter is disclosed. The coupler assembly includes a coupler, an ultrasonic transducer array coupled to the coupler, first and second magnetic positioning sensors, and a pull-ring. The first and second magnetic positioning sensors are coupled to the coupler at nonparallel orientations relative to one another, and transmit an electrical signal indicative of the six degrees of freedom that the ultrasonic transducer array has within a controlled magnetic field. The pull-ring is coupled to the coupler and one or more steering wires. The pull-ring and the one or more steering wires facilitate steering the intravascular catheter via actuation of the one or more steering wires. In more specific implementations, the ultrasonic transducer array includes a backing/insulating layer sandwiched between a plurality of ultrasonic transducers and a flexible electronic circuit. The flexible electronic circuit is electrically coupled to each of the plurality of ultrasonic transducers in the array, and the insulating layer absorbs noise that is emitted from a back-side of the ultrasonic transducers.

The foregoing and other aspects, features, details, utilities, and advantages of the present disclosure will be apparent from reading the following description, and from reviewing the accompanying drawings.

BRIEF DESCRIPTION OF THE DRAWINGS

Various example embodiments may be more completely understood in consideration of the following detailed description in connection with the accompanying drawings.

Figure 1A:
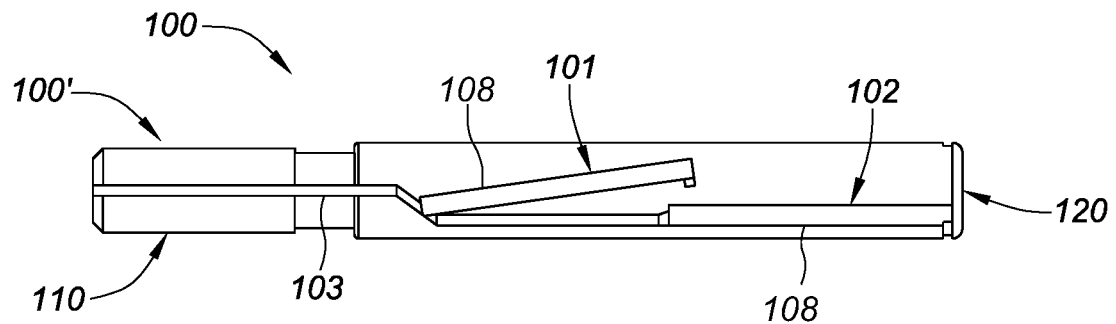
FIG. 1A is a top plan view of a partial coupler assembly of an ultrasonic transducer array catheter, consistent with various embodiments of the present disclosure.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION OF EMBODIMENTS

Aspects of the present disclosure are directed to an intravascular catheter with a coupler at a distal end which facilitates precise and efficient positioning of an ultrasonic transducer array and one or more magnetic localization sensors (also referred to herein as magnetic position sensors).

Various aspects of the present disclosure are directed to methods of manufacturing an ultrasonic transducer array catheter. Some methods of manufacturing include utilizing a coupler at a distal end of the catheter that facilitates precise assembly and relative positioning of at least one of: steering components, an ultrasonic transducer array, and magnetic localization sensors therein.

Various embodiments of the present disclosure are directed to a coupler for use near a distal tip of a catheter. Such a coupler may facilitate coupling a catheter shaft to various components at the distal tip of the catheter. For example, the coupler may precisely orient and position one or more magnetic position sensors, thermistor (or thermocouple), and an ultrasonic transducer array. In various embodiments, the coupler is the chassis upon which other components of a distal tip subassembly are mounted to improve catheter assembly efficiency. Moreover, the coupler may be further designed to facilitate coupling of a pull-ring of a mechanical catheter steering system thereto. Also, the coupler may include proximal end features that facilitate joining the distal tip subassembly with a catheter shaft assembly.

Aspects of the various couplers disclosed herein may be particularly relevant to catheter applications that rely upon magnetic localization sensors to determine a position of the catheter within a cardiovascular system of a patient (among other applications). For example, in some magnetic localization systems, the system must include one or more magnetic positioning sensors within the catheter tip that must be precisely positioned relative to other components of the catheter or one or more other magnetic positioning sensors. Where the catheter is an ultrasound imaging catheter, the perceived relative location and known relative location of the magnetic positioning sensor(s) and the ultrasonic transducer (array) may require precise alignment. Additionally, coupler design disclosed herein ensures that the magnetic positioning sensors are placed accurately each time during assembly, and may also be used during manufacturing to aid proper placement of a thermistor (or temperature sensor) and a transducer array assembly. The coupler may also serve as a structural member of the catheter, increasing strength of a distal tip subassembly both during manufacturing and use. In some embodiments, the coupler may integrate several components of an ultrasound catheter tip structure to reduce part count and assembly complexity.

Embodiments of the present disclosure are directed to a coupler for an intravascular catheter with an ultrasonic transducer array at a distal tip. The coupler is configured to hold a six degrees of freedom (DOF) sensor assembly, which includes a pair of magnetic position sensors. Each of the magnetic position sensors may include a coil wound around a longitudinal axis. In some embodiments, the magnetic position sensors may be elongated. The coupler may include sensor grooves formed in an outer portion of the coupler, in which the six degrees of freedom sensor assembly can be placed. The magnetic position sensors may be offset by a particular angle from a longitudinal axis due to where the sensor grooves are formed in the coupler. Each sensor can be offset by the particular angle with respect to the longitudinal axis formed by the coupler, causing the two five DOF sensors when combined to form a six DOF sensor assembly. The six DOF sensor assembly may sense position (e.g., x, y, z) and orientation (e.g., roll, pitch, yaw). For example, because the two magnetic position sensors are at a slight angle with respect to one another, they can be at different rotational angles with respect to the axis of the magnetic field. Thus, as the magnetic position sensors rotate in any angle, the difference in voltage, and also their vectors can be picked up and consequently, a six DOF sensor can be created.

In some embodiments, sensor grooves in the coupler may be offset by a particular angle with respect to a coupler longitudinal axis and can be diametrically opposed to one another. By doing so, magnetic position sensors inserted into the sensor grooves and thus set at an appropriate angle with respect to one another enable two five DOF magnetic position sensors to act as a six DOF sensor assembly. In an example, the first sensor groove can be disposed at a positive 5 degree angle, with respect to the longitudinal axis, and the second sensor groove can be disposed at a negative 5 degree angle, relative to the longitudinal axis, to create a 10 degree separation between the magnetic position sensors. In some embodiments, the degree of separation between the magnetic position sensors and sensor grooves can be in a range from 1 degree to 20 degrees, 5 degrees to 15 degrees, and preferably from 10 degrees to 12 degrees. However, the degree of separation can be less than 1 degree or over 20 degrees, in some embodiments. In other embodiments, each of the magnetic position sensors and sensor grooves can be disposed at a same angle with respect to the longitudinal axis. In yet other embodiments, one of the magnetic position sensors and sensor grooves can be disposed at a greater angle than the other magnetic position sensors and sensor grooves; however, the degree of separation between the magnetic position sensors and sensor grooves can still be within the ranges discussed herein.

Aspects of the present disclosure are further directed to a sensor coupler assembly. The sensor coupler assembly includes a coupler body that facilitates coupling of an ultrasonic transducer array to a catheter shaft. The coupler may be adapted to facilitate the mounting of magnetic localization coils (magnetic position sensors) to grooves extending into an outer diameter of the coupler body. When located within a controlled magnetic field, the pair of magnetic localization coils produce an electrical signal that is indicative of the six degrees of freedom that the catheter tip has within space. In some advanced embodiments, the location of the catheter tip may be associated with a position within a patient's anatomy and displayed for the clinician to reference during a procedure. A display communicatively coupled to localization system controller circuitry may transmit data packets to the display indicative of the location of the ultrasonic transducer array within the controlled magnetic field.

To facilitate the coupling of a coupler body to an external housing, inverted radiuses in an outer diameter of the coupler body may be utilized to facilitate flow of adhesive in and around the coupler when being coupled with an external housing. The inverted radiuses may also house, for example, electrical wiring such as ring electrode wires extending between ring electrodes near a distal tip of the catheter and a catheter handle.

The relatively proximal placement of the coupler body relative to a distal tip of the catheter allows for accurate magnetic localization of the catheter tip via magnetic localization coils within the coupler body.

Various aspects of the present disclosure are directed to a coupler for a distal sub-assembly of a catheter that integrates a pull-ring thereon. To alleviate size constraints of a catheter, condensing the number of components at a distal tip of the catheter is desirable. In some embodiments, a coupler is disclosed that secures one or more magnetic positioning sensors at precise locations within the distal tip and also holds a pull-ring for a steering system in place. This integration of various components on to the coupler allows for a reduction in the total length of the catheter distal to the pull-ring; more importantly, this may allow for desirable sweep characteristics in response to a clinician's steering input.

A coupler may include a pull-ring groove that mates to one or more features of a pull-ring. In one embodiment of such a coupler, the proximal portion of the coupler has a reduced diameter compared to a distal portion, and is non-coaxial with the distal portion of the coupler. This coupler shape facilitates a pull-ring extending around the proximal portion of the coupler, and to interface with a groove thereon—thereby securing the pull-ring to the coupler. Once the distal tip assembly is over molded, the pull-ring is laterally held in place, and forces exerted on the pull-ring (e.g., in response to a clinician's steering input) are translated to the coupler to effect a desired sweep. In such an embodiment, the catheter may not bend distal to a proximal edge of the coupler (where the coupler is rigid); however, positioning the pull-ring relatively distal on the distal tip subassembly allows for a durometer transition of Pebax® on a proximal end of the coupler. This durometer transition may be particularly desirable where flexibility of the catheter shaft is desirable, but durability is preferred at the distal tip. Accordingly, such a catheter including the coupler is capable of deflecting over a longer length, and at a more distal location—reducing a sweep of the catheter. In some embodiments, this sweep reduction may be even more than a sweep reduction produced by shortening a section length of the catheter. As will be discussed in more detail in reference to FIG. 9A, a pull-ring groove 917 may be positioned proximal to an angled section 906 of a coupler 900 to reduce stress concentrations therein associated with catheter guidewire manipulation.

Details of the various embodiments of the present disclosure are described below with specific reference to the figures.

FIG. 1A is a top plan view of a partial coupler assembly 100 of an ultrasonic transducer array catheter, consistent with various embodiments of the present disclosure. The partial coupler assembly 100 includes a coupler 100' with one or more pathways 103 that facilitate the routing of electrical conductors to, and from, electrical components mounted to the coupler 100'. In FIG. 1A, magnetic sensors 101 and 102 are placed within trenches 108 which extend into a top surface of the coupler 100'. Electrical conductors extending from the magnetic sensors 101 and 102 may be routed through pathway 103 and a lumen of the catheter shaft to a proximal end of the catheter where the electrical conductors are coupled to controller circuitry, for example. The trenches within the top surface of the coupler 100' facilitate precise positioning of the magnetic sensors relative to one another and the distal tip of the catheter. In some applications, for example, the magnetic sensors must be positioned with a precise angle relative to one another to facilitate a magnetic localization system detecting each of the catheter tip's six degrees of freedom.

As further shown in FIG. 1A, some embodiments of a coupler 100' have a proximal portion 110 with a reduced diameter relative to a distal portion 120. Moreover, for facilitating coupling of a pull-ring to the coupler, some embodiments have non-coaxial proximal and distal portions of the coupler 100'.

Figure 1B:
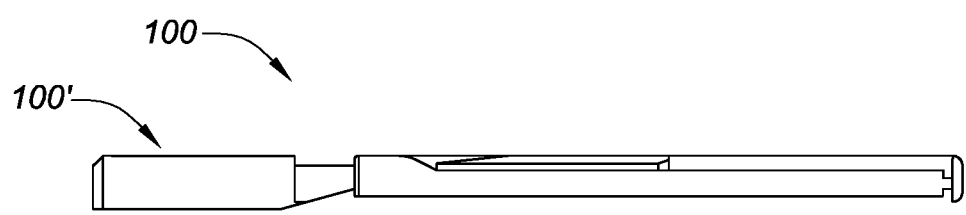
FIG. 1B is a left plan view of the partial coupler assembly of FIG. 1A, consistent with various embodiments of the present disclosure.

FIG. 1B is a left plan view of the partial coupler assembly 100 of FIG. 1A including coupler 100', consistent with various embodiments of the present disclosure.

Figure 1C:
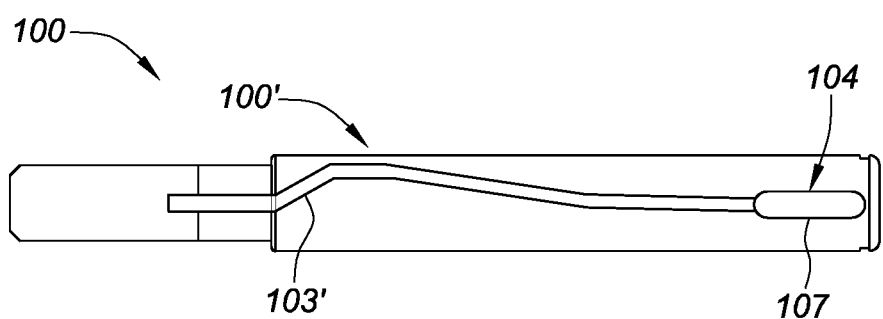
FIG. 1C is a bottom plan view of the partial coupler assembly of FIG. 1A, consistent with various embodiments of the present disclosure.

FIG. 1C is a bottom plan view of the partial coupler assembly 100 of FIG. 1A, consistent with various embodiments of the present disclosure. In FIG. 1C, the partial coupler assembly 100 includes coupler 100' with a second pathway 103' for facilitating the routing of electrical conductors to, and from, a thermistor 104 mounted near a distal end of the coupler 100'. In FIG. 1C, the thermistor is placed within a trench 107 that extends into a bottom surface of the coupler 100'. One or more electrical conductors extending from the thermistor 104 may be routed through pathway 103' and a lumen of the catheter shaft to a proximal end of the catheter where the one or more electrical conductors are coupled to controller circuitry, for example.

Figure 1D:
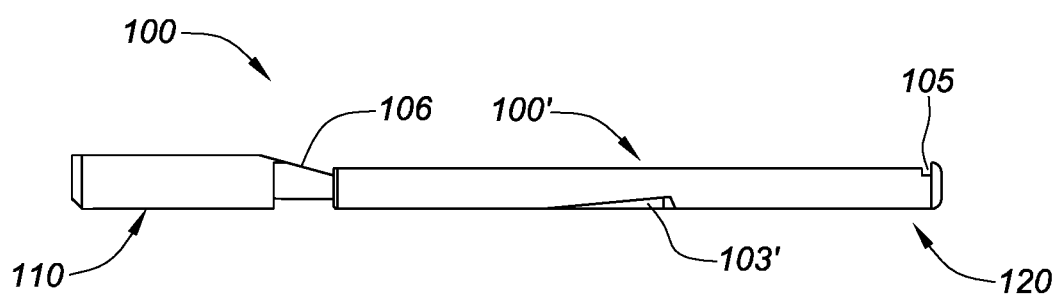
FIG. 1D is a right plan view of the partial coupler assembly of FIG. 1A, consistent with various embodiments of the present disclosure.

FIG. 1D is a right plan view of the partial coupler assembly 100 of FIG. 1A and includes a coupler 100', consistent with various embodiments of the present disclosure. FIG. 1D also partially shows the pathway 103' extending to the thermistor 104. As further shown in FIG. 1D, a ramp 106 between proximal and distal portions, 110 and 120, respectively, of coupler 100' facilitates a non-coaxial arrangement between the two portions. The ramp 106 may also facilitate a cavity in the distal portion 120 for an ultrasonic transducer array. In such an arrangement, the ramp 106 provides a gradual transition between the cavity and a top surface of the coupler. This gradual transition may be particularly useful for routing electrical conductors and flexible circuits without over-flexing, which may otherwise result in cracks or other discontinuities in the conductors. Moreover, the coupler 100' further includes an engagement feature 105 that facilitates precise locating and coupling of an ultrasonic transducer array to the coupler 100'.

Figure 2A:
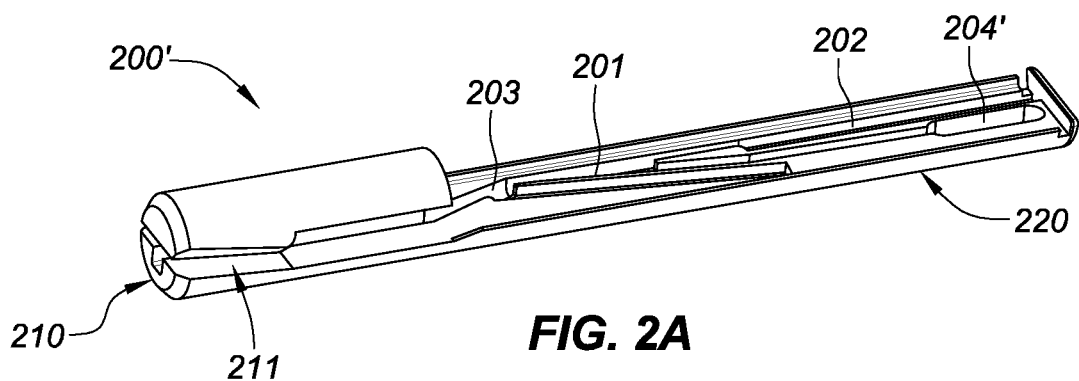
FIG. 2A is an isometric top view of a coupler for an ultrasonic transducer array catheter, consistent with various embodiments of the present disclosure.

FIG. 2A is an isometric top view of a coupler 200' for an ultrasonic transducer array catheter, consistent with various embodiments of the present disclosure. As shown in FIG. 2A, the coupler 200' includes a proximal portion 210 and a distal portion 220. The distal portion 220 includes trenches 201, 202, and 204' for precise assembly and coupling of magnetic sensors and thermistor(s) (or thermal sensors) to the coupler 200'. Wiring for the magnetic sensors and thermistor run through a shared pathway 203 that extends along a length of a top surface of the coupler 200'. An undercut 211 in the proximal portion 210 of the coupler 200' facilitates a pathway 203 for wires and flexible circuits. As will be discussed in more detail below, the undercut 211 and engagement feature 205 (as shown in FIG. 2E) may be used to couple an ultrasonic transducer array to the coupler 200'. In various embodiments, the undercut and engagement feature may also be supplemented with fasteners, adhesive, and/or over molding of the entire distal-tip assembly.

Figure 2B:
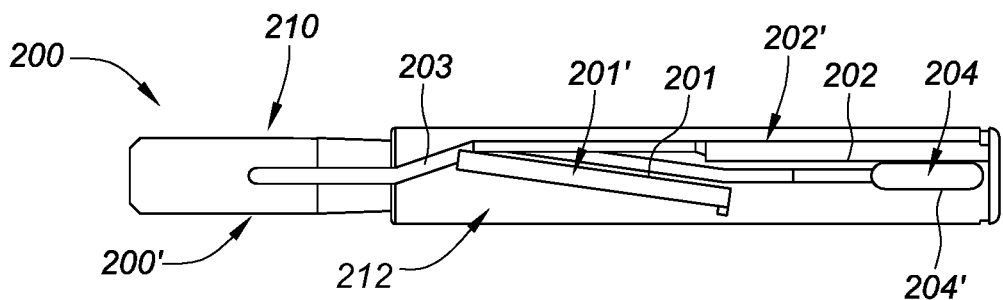
FIG. 2B is a top plan view of a partial coupler assembly for an ultrasonic transducer array catheter, consistent with various embodiments of the present disclosure.

FIG. 2B is a top plan view of a partial coupler assembly 200 for an ultrasonic transducer array catheter, consistent with various embodiments of the present disclosure. As shown in FIG. 2B, magnetic sensors 201' and 202' are placed within trenches 201 and 202, respectively. The trenches 201 and 202 extend along a length of a top surface 212 of the coupler 200'. Similarly, a thermistor 204 is placed within trench 204'. The wires for each are then routed along a shared pathway 203 toward a proximal portion 210 of the coupler 200'.

Figure 2C:
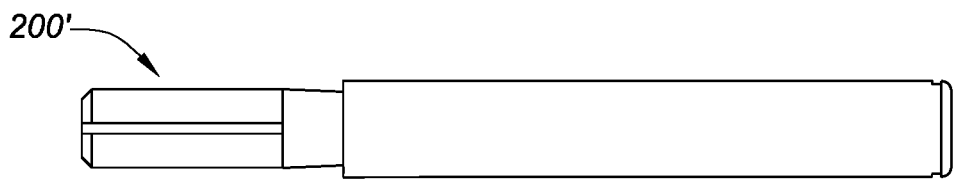
FIG. 2C is a bottom plan view of the coupler of FIG. 2A, consistent with various embodiments of the present disclosure.
Figure 2D:
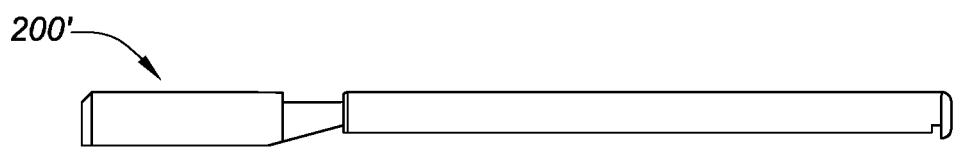
FIG. 2D is a right plan view of the coupler of FIG. 2A, consistent with various embodiments of the present disclosure.
Figure 2E:
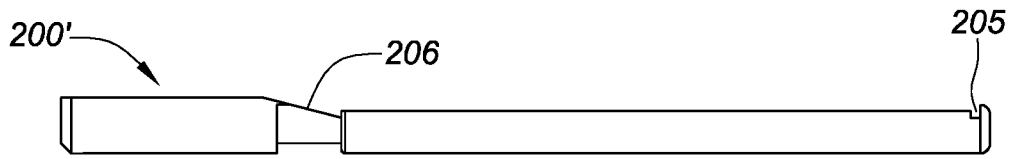
FIG. 2E is a left plan view of the coupler of FIG. 2A, consistent with various embodiments of the present disclosure.

FIG. 2C is a bottom plan view of the coupler 200' of FIG. 2A, FIG. 2D is a left plan view of the coupler 200' of FIG. 2A, and FIG. 2E is a right plan view of the coupler 200' of FIG. 2A, consistent with various embodiments of the present disclosure.

As further shown in FIG. 2E, a ramp 206 between proximal and distal portions, 210 and 220, respectively, of coupler 200' facilitates a non-coaxial arrangement between the two portions. The ramp 206 may also facilitate a cavity in the distal portion 220 for an ultrasonic transducer array. In such an arrangement, the ramp 206 provides a gradual transition between the cavity and a top surface of the coupler. This gradual transition may be particularly useful for routing electrical conductors and flexible circuits without over-flexing, which may otherwise result in cracks or other discontinuities in the conductors. Moreover, the coupler 200' further includes an engagement feature 205 that facilitates precise locating and coupling of an ultrasonic transducer array to the coupler 200'.

Figure 3A:
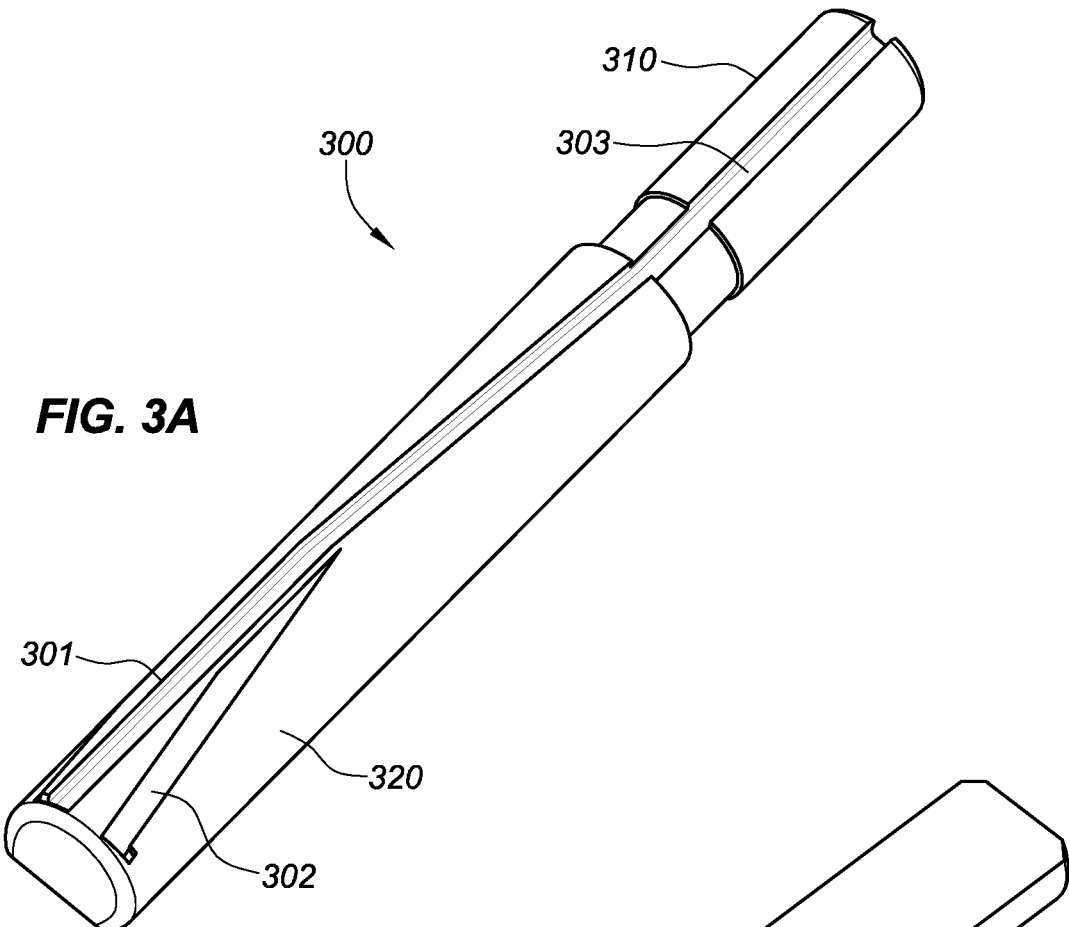
FIG. 3A is an isometric bottom view of a coupler for an ultrasonic transducer array catheter, consistent with various embodiments of the present disclosure.

FIG. 3A is an isometric bottom view of a coupler 300 for an ultrasonic transducer array catheter, consistent with various embodiments of the present disclosure. As shown in FIG. 3A, trenches 301 and 302 facilitate placement of magnetic sensors therein, and an electrical pathway 303 which extends into a circumferential bottom surface of the coupler 300 (and through proximal portion 310 into distal portion 320) facilitates routing of electrical conductors therein. The trenches 301 and 302 are positioned in a distal portion 320 of the coupler 300, with the two trenches angled relative to one another. The relative angle of the magnetic positioning sensors may be necessary in some magnetic localization systems to facilitate desired detection of all six degrees of freedom of a catheter's distal tip.

Figure 3B:
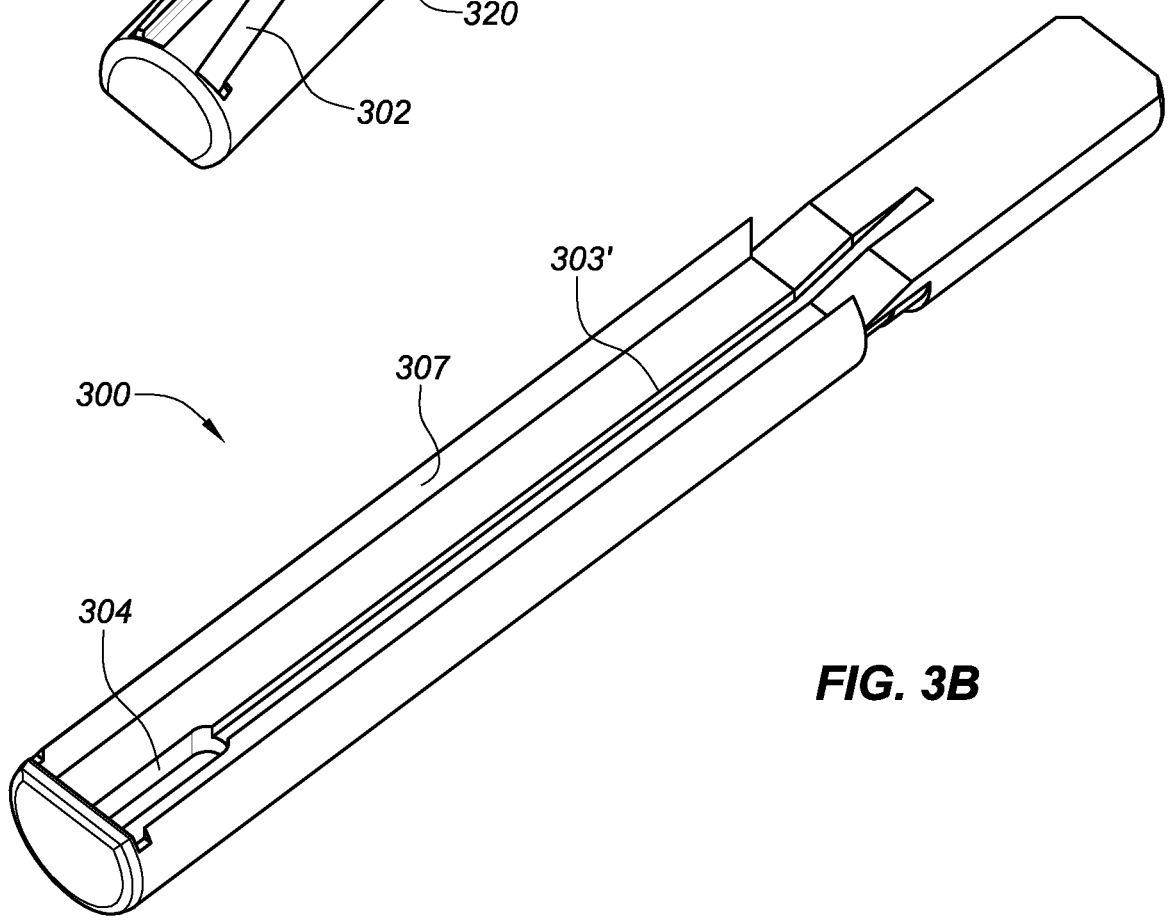
FIG. 3B is an isometric top view of the coupler of FIG. 3A, consistent with various embodiments of the present disclosure.

FIG. 3B is an isometric top view of the coupler 300 of FIG. 3A, consistent with various embodiments of the present disclosure. In FIG. 3B, a cavity 307 extends into a top surface of the coupler 300. The cavity 307 facilitates positioning and joining of an ultrasonic transducer array to the coupler 300. A thermistor trench 304 extends further into the cavity 307, so that a final position of a thermistor within the trench 304 does not interfere with placement of the ultrasonic transducer array within the cavity. Similarly, pathway 303' facilitates routing of electrical conductors from the thermistor along a length of the coupler 300, below the ultrasonic transducer assembly.

Figure 4A:
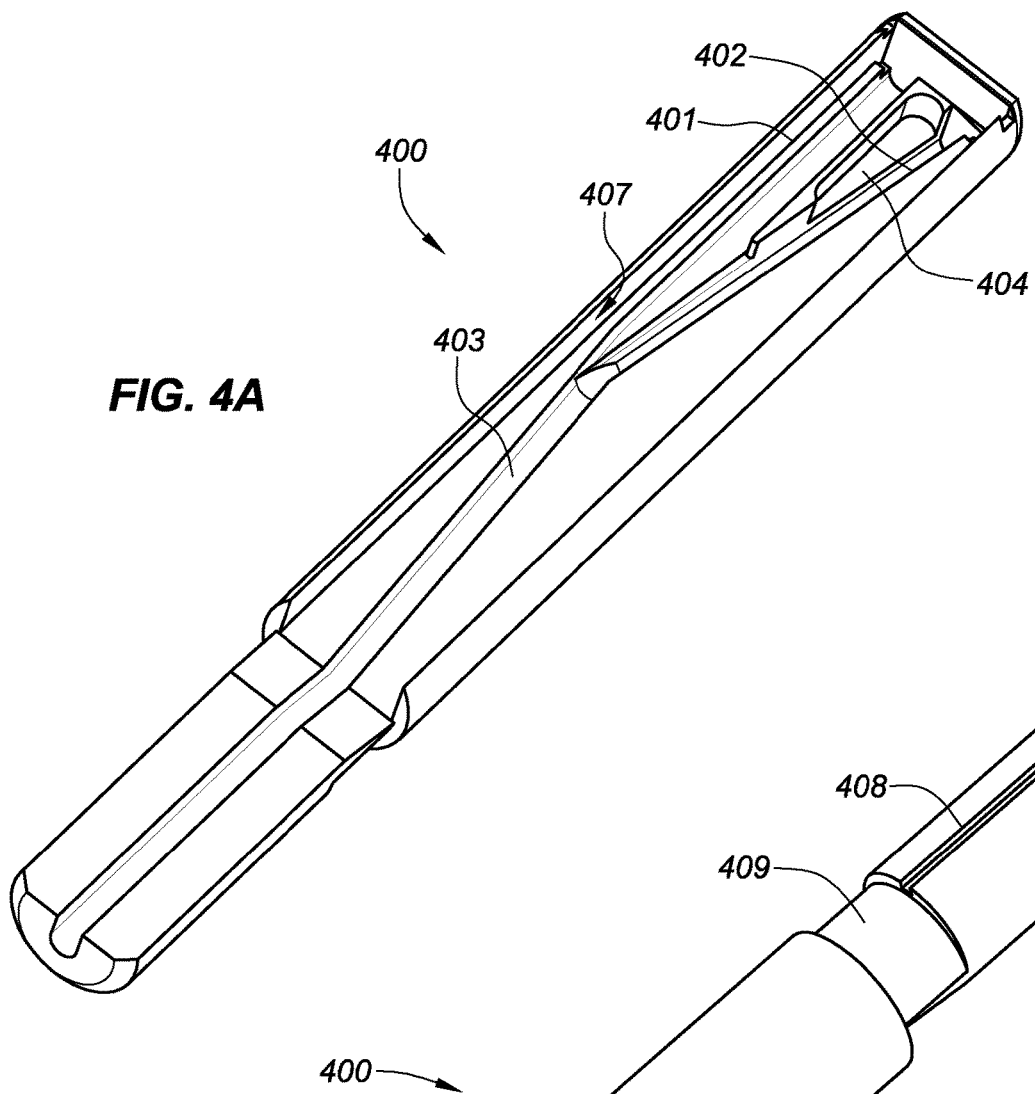
FIG. 4A is an isometric top view of a coupler for an ultrasonic transducer array catheter, consistent with various embodiments of the present disclosure.

FIG. 4A is an isometric top view of a coupler 400 for an ultrasonic transducer array catheter, consistent with various embodiments of the present disclosure. Trenches 401, 402, and 404 for two magnetic sensors and a thermistor, respectively, share a common pathway 403 for electrical conductors extending therefrom. A cavity 407 extends into a top surface of the coupler 400. The cavity 407 facilitates positioning and securing of an ultrasonic transducer array to the coupler 400. The trenches 401, 402, and 404 extend into a bottom surface of the cavity 407 to a sufficient depth to prevent obstruction to the interface between the ultrasonic transducer array and the cavity 407.

Figure 4B:
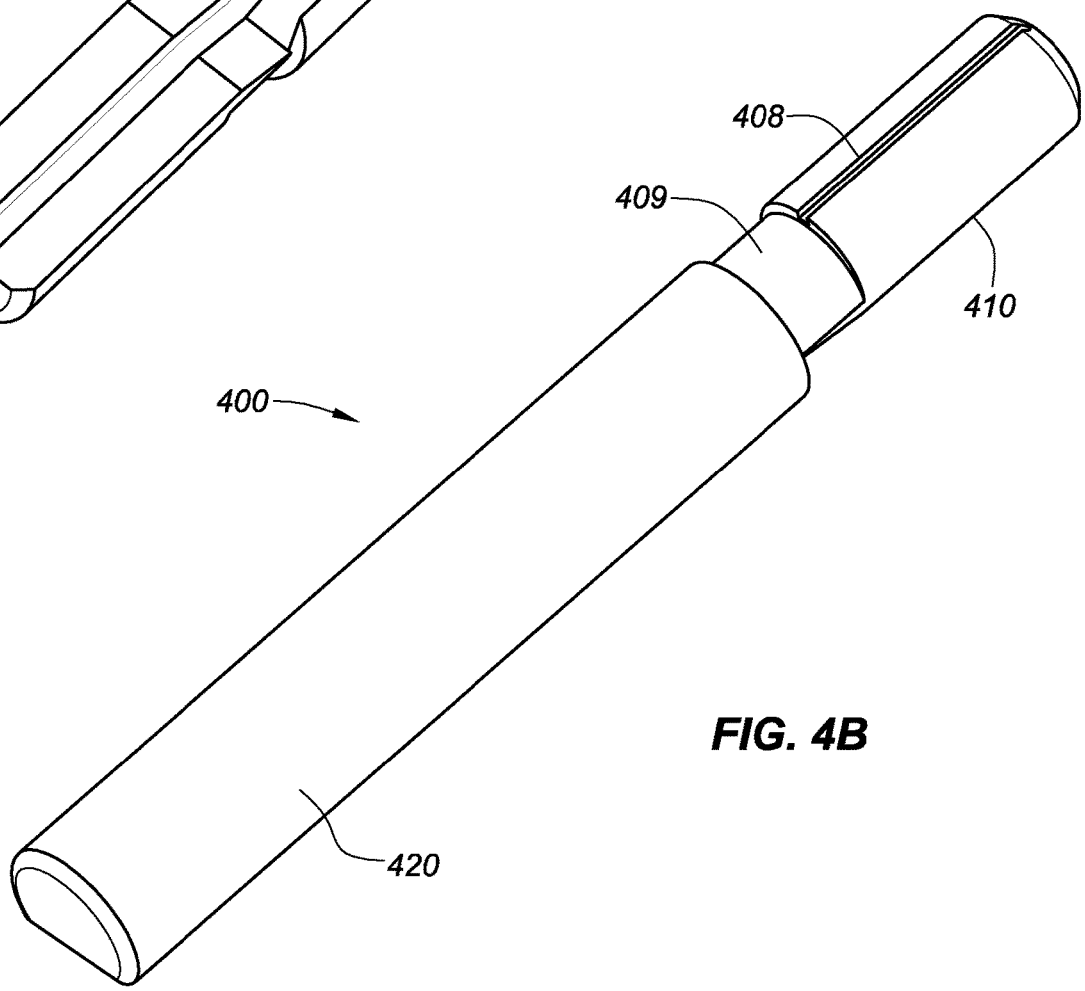
FIG. 4B is an isometric bottom view of the coupler of FIG. 4A, consistent with various embodiments of the present disclosure.

FIG. 4B is an isometric bottom view of the coupler 400 of FIG. 4A, consistent with various embodiments of the present disclosure. A proximal portion 410 of the coupler 400 may include a keyway 408 to facilitate proper alignment of a distal tip assembly relative to a catheter shaft during assembly. In the present embodiment, a pull-ring groove 409 is positioned between the proximal and distal portions, 410 and 420, respectively. The pull-ring groove 409 facilitates securing a pull-ring (part of a steering system assembly for the catheter) to the coupler 400.

Figure 5A:
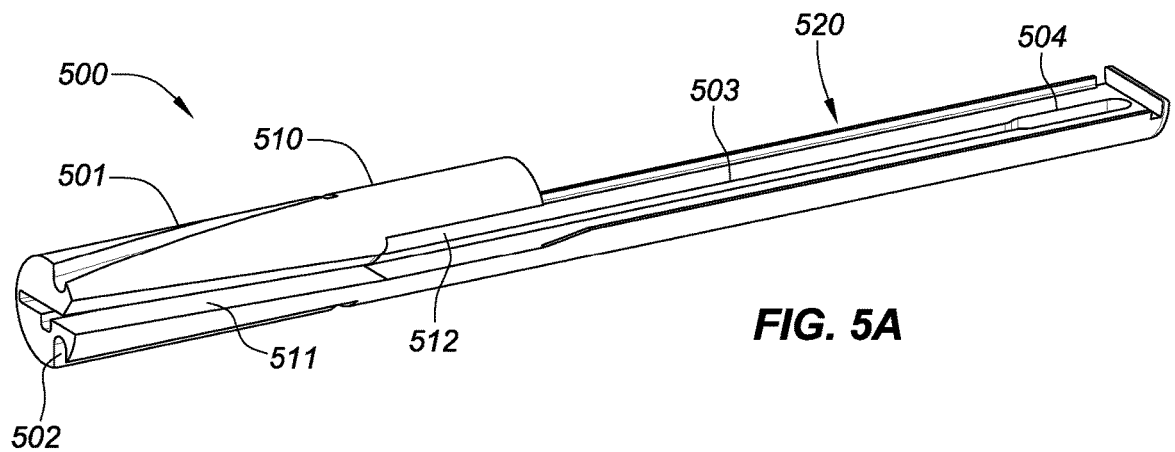
FIG. 5A is an isometric top view of a coupler for an ultrasonic transducer array catheter, consistent with various embodiments of the present disclosure.

FIG. 5A is an isometric top view of a coupler 500 for an ultrasonic transducer array catheter, consistent with various embodiments of the present disclosure. As shown in FIG. 5A, a distal portion 520 of the coupler 500 includes a trench 504 for a thermistor and a pathway 503 for electrical conductors extending therefrom. At a proximal portion 510 of the coupler 500, trenches 501 and 502 extend along a length of a circumferentially extending outer surface. To facilitate measuring six degrees of freedom from the two magnetic sensors, a first trench 502 extends collinear with a longitudinal axis of the coupler 500, while a second trench 501 extends at an angle relative to the longitudinal axis of the coupler 500. The proximal portion 510 further includes an interface feature 512 for facilitating the coupling of an ultrasonic transducer array to the coupler 500. An undercut feature 511 facilitates the manufacturability of the pathway 503 through the coupler 500.

Figure 5B:
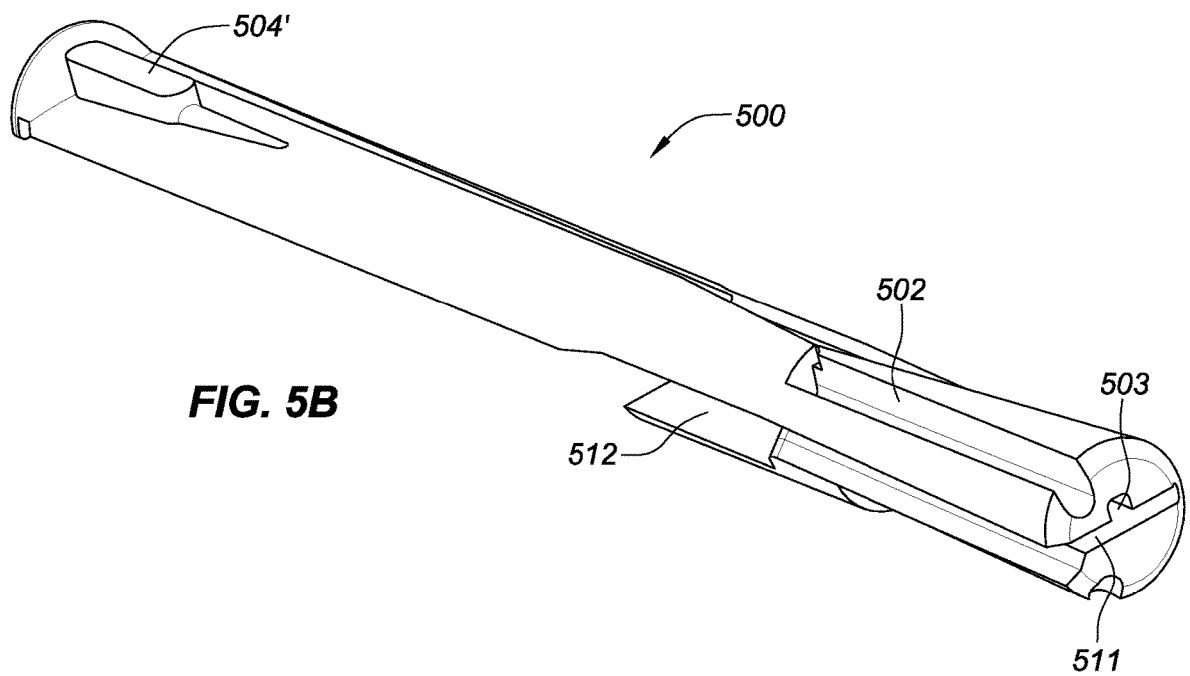
FIG. 5B is an isometric bottom view of the coupler of FIG. 5A, consistent with various embodiments of the present disclosure.
Figure 5C:
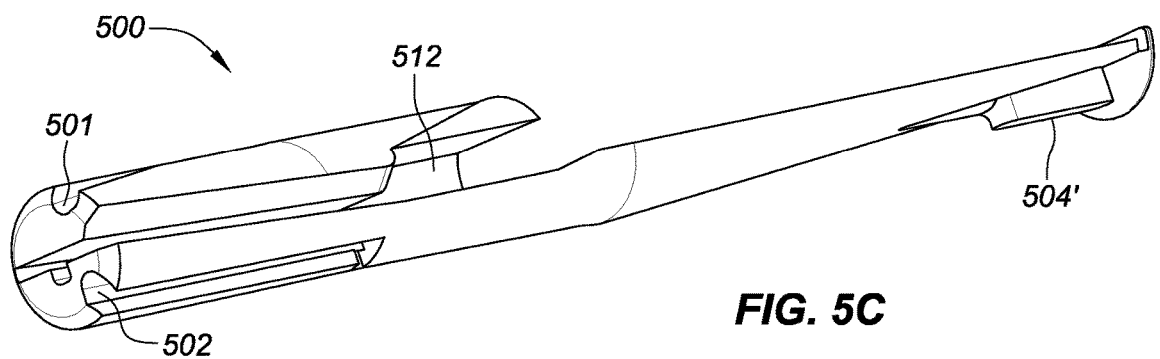
FIG. 5C is an isometric side view of the coupler of FIG. 5A, consistent with various embodiments of the present disclosure.

FIG. 5B is an isometric bottom view of the coupler 500 of FIG. 5A, consistent with various embodiments of the present disclosure. FIG. 5C is an isometric side view of the coupler of FIG. 5A, consistent with various embodiments of the present disclosure. To allow for a desirable depth of trench 504, a trench boss 504' extends out beyond the outer diameter of the distal portion 520.

Figure 6A:
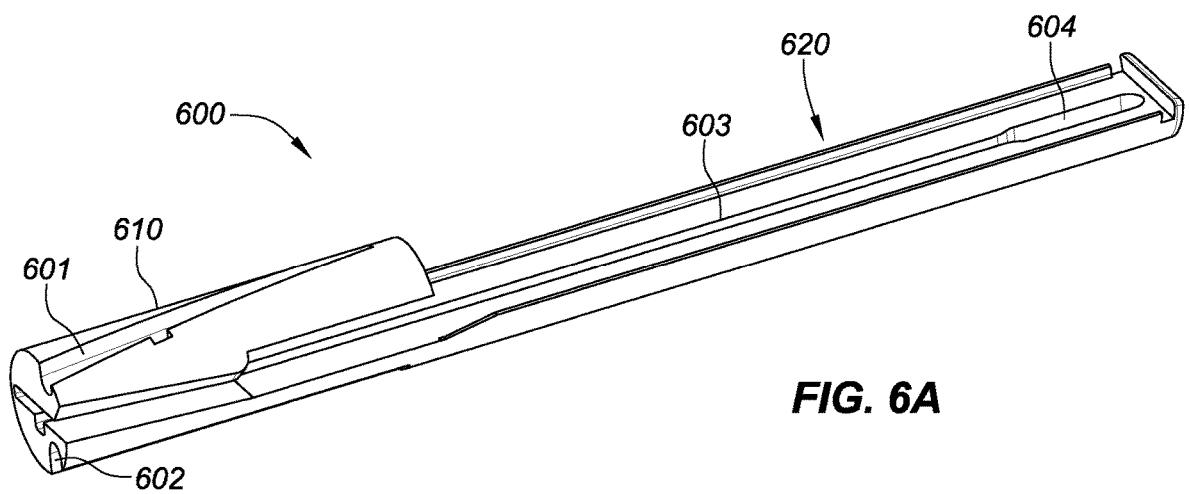
FIG. 6A is an isometric top view of a coupler for an ultrasonic transducer array catheter, consistent with various embodiments of the present disclosure.

FIG. 6A is an isometric top view of a coupler 600 for an ultrasonic transducer array catheter, consistent with various embodiments of the present disclosure. As shown in FIGS.

6B-C interface feature 612 of proximal portion 610 is longitudinally shortened relative to the interface feature 512 of FIGS. 5A-C.

As shown in FIG. 6A, a distal portion 620 of the coupler 600 includes a trench 604 for a thermistor, and a pathway 603 for electrical conductors extending therefrom. At a proximal portion 610 of the coupler 600, trenches 601 and 602 extend along a length of a circumferentially extending outer surface. To facilitate measuring six degrees of freedom from the two magnetic sensors (as discussed in more detail earlier), a first trench 602 extends collinear with a longitudinal axis of the coupler 600, while a second trench 601 extends at an angle relative to the longitudinal axis of the coupler 600.

Figure 6B:
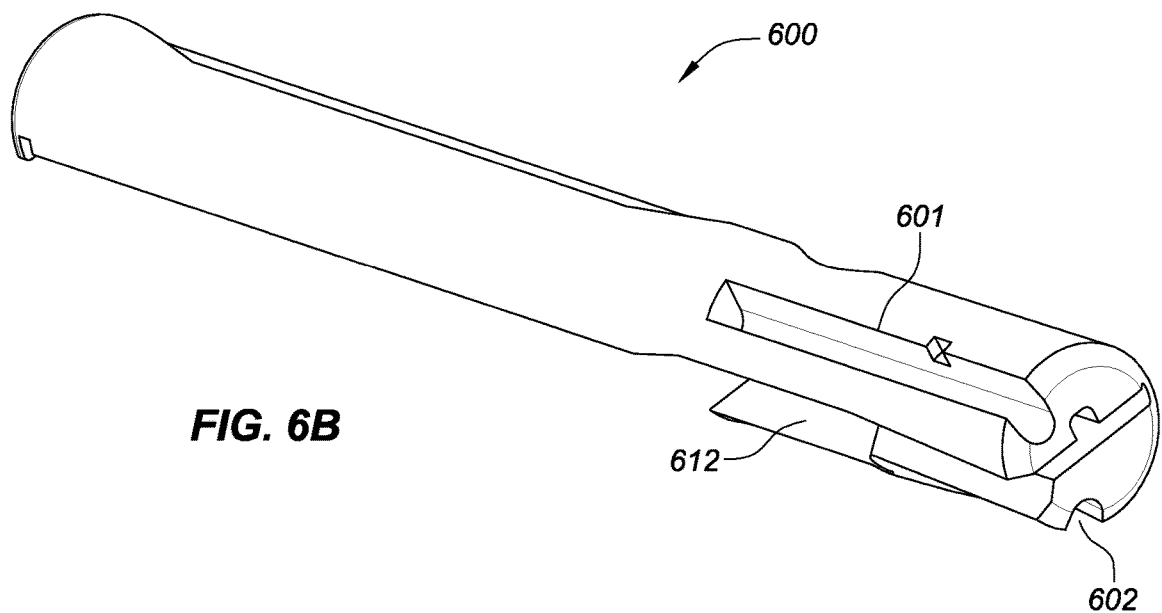
FIG. 6B is an isometric bottom view of the coupler of FIG. 6A, consistent with various embodiments of the present disclosure.

FIG. 6B is an isometric bottom view of the coupler 600 of FIG. 6A, consistent with various embodiments of the present disclosure. As shown in FIG. 6B, a proximal portion 610 of coupler 600 includes an interface feature 612 that facilitates coupling an ultrasonic transducer array to the coupler 600.

Figure 6C:
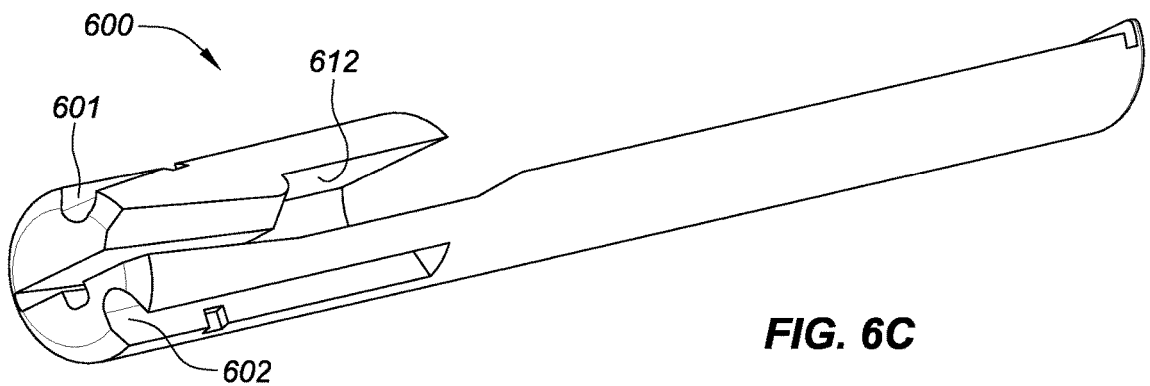
FIG. 6C is an isometric side view of the coupler of FIG. 6A, consistent with various embodiments of the present disclosure.

FIG. 6C is an isometric side view of the coupler 600 of FIG. 6A, consistent with various embodiments of the present disclosure. In various embodiments of the present disclosure, interface feature 612 allows for backing/insulative material and/or flexible circuitry of an ultrasonic transducer array assembly to extend into a cavity of the coupler defined by the interface feature 612. The interface feature 612 may also support a portion of the ultrasonic transducer array that extends distal the interface.

Figure 7:
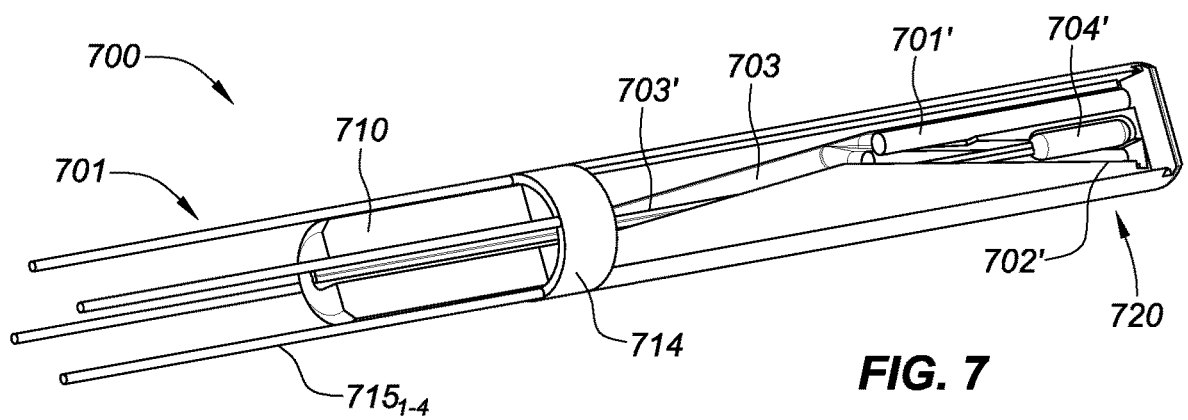
FIG. 7 is an isometric top view of a partial coupler assembly of an ultrasonic transducer array catheter, consistent with various embodiments of the present disclosure.

FIG. 7 is an isometric top view of a partial coupler assembly 701 (also referred to herein as a distal tip subassembly) of an ultrasonic transducer array catheter, consistent with various embodiments of the present disclosure. As shown in FIG. 7, magnetic sensors 701' and 702', and thermistor 704' have been mounted to trenches within a top surface of coupler 700. Electrical conductors 703' extending from the magnetic sensors and thermistor may be routed via pathway 703 to a proximal portion 710 of coupler 700. A pull-ring 714 may be secured to the coupler 700 at an interface between the proximal portion 710 and a distal portion 720 of the coupler. One or more guidewires 715$_{1-4}$ extend a length of the catheter shaft between the pull-ring 714 and a catheter handle, and are manipulated by the catheter handle to create various sweeping profiles of the catheter shaft—thereby facilitating steering of the distal tip of the catheter during an intravascular procedure.

Figure 8A:
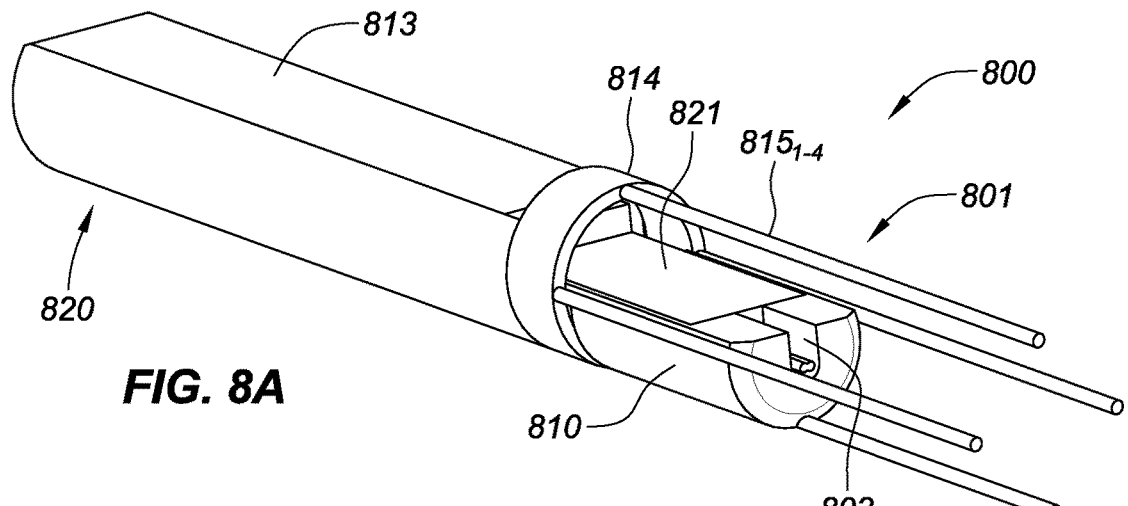
FIG. 8A is an isometric top view of a complete distal tip sub-assembly of an ultrasonic transducer array catheter, consistent with various embodiments of the present disclosure.

FIG. 8A is an isometric top view of a complete distal tip subassembly 801 of an ultrasonic transducer array catheter, consistent with various embodiments of the present disclosure. The subassembly 801 is shown prior to being fastened to a catheter shaft assembly, and before over molding the tip (e.g., in silicone, or sliding a Pebax® sleeve over the subassembly). An ultrasonic transducer array 813 is coupled to a distal portion 820 of coupler 800. A flexible circuit 821, electrically coupled to the ultrasonic transducer array 813, extends proximally. The flexible circuit 821 may extend proximal to a proximal portion 810 of the coupler 800, and facilitate the communication of electrical signals to, and from, the ultrasonic transducer array 813. In some embodiments, the flexible circuit 821 may extend a length of the catheter shaft, or include solder pads which facilitate soldering electrical conductors to the flexible circuit—the electrical conductors extending a remaining length of the catheter shaft. To facilitate manufacturing, the ultrasonic transducer array 813, the flexible circuit 821, and optionally an insulative material therebetween may be pre-packaged.

The ultrasonic transducer array assembly may then be assembled into the coupler 800.

A pull-ring 814 may be secured to one or more features of the coupler 800. In some embodiments, the pull-ring 814 may be proximal ultrasonic transducer array 813. The pull-ring 814 may be secured at an interface between a proximal portion 810 and a distal portion 820 of the coupler 800. The pull-ring 814 may mate with one or more features of the coupler 800 to prevent relative movement of the pull-ring and coupler 800 during use. One or more guidewires 815$_{1-4}$ extend a length of the catheter shaft (via one or more lumens therein) between the pull-ring 814 and a catheter handle.

Figure 8B:
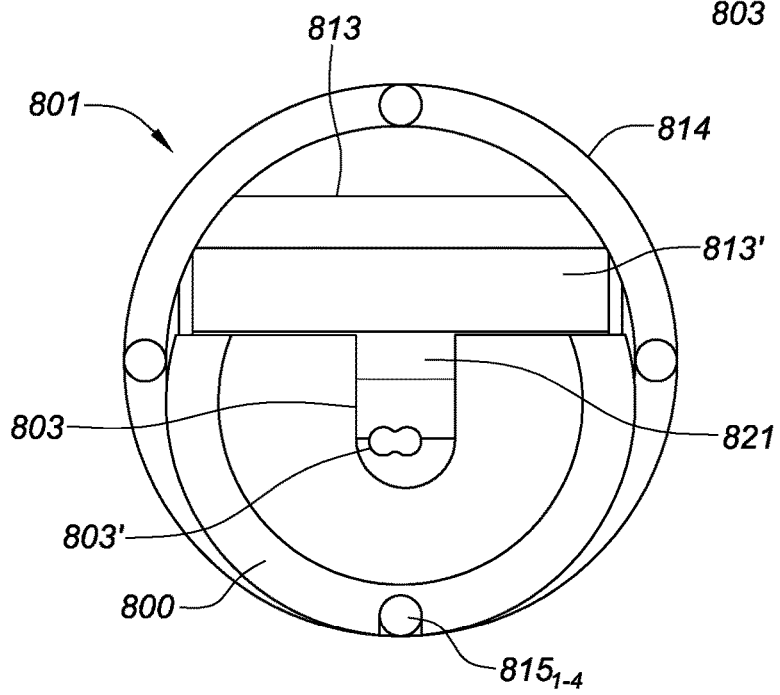
FIG. 8B is front plan view of the complete distal tip sub-assembly of FIG. 8A, consistent with various embodiments of the present disclosure.

FIG. 8B is a front plan view of the complete distal tip sub-assembly 801 of FIG. 8A, consistent with various embodiments of the present disclosure. An ultrasonic transducer array 813 which is secured to the coupler 800 may also include a backing/insulating layer 813', which is sandwiched between both the ultrasonic transducer array 813 and a flexible circuit 821. The flexible circuit 821 is electrically coupled to each of the ultrasonic transducers in the array 813. In various embodiments, the insulating layer 813' may absorb noise that is emitted from the back-side of the ultrasonic transducers in the array 813. Absent the backing layer 813', the noise from each of the ultrasonic transducers may re-bound off the flexible circuit 821, and be detected by the one or more ultrasonic transducers as a portion of a signal image—negatively impacting the clarity of the post-processed image.

Electrical conductors 803' extending from the magnetic sensors and thermistor may be routed via pathway 803 to a proximal portion 810 of coupler 800.

In one specific embodiment of the present disclosure, a complete coupler assembly includes magnetic sensors, and a thermistor secured to a coupler via trenches. Electrical conductors from each of the magnetic sensors, and thermistor are routed proximally along a pathway cut into an outer diameter of the coupler. A flexible circuit extends over a top surface of the coupler and is electrically coupled to an ultrasonic transducer array which includes a backing/insulating layer sandwiched between the flexible circuit and an array of ultrasonic transducers coupled to a top surface of the backing/insulating layer. The backing/insulating layer and the flexible circuit may extend proximally into an interfacing portion of the coupler to mechanically support the portion of the ultrasonic transducer array that extends distally. The coupler assembly and the rest of the distal tip of the catheter may then be over molded (e.g., with silicone, Pebax®, or other FDA approved material).

Figure 9A:
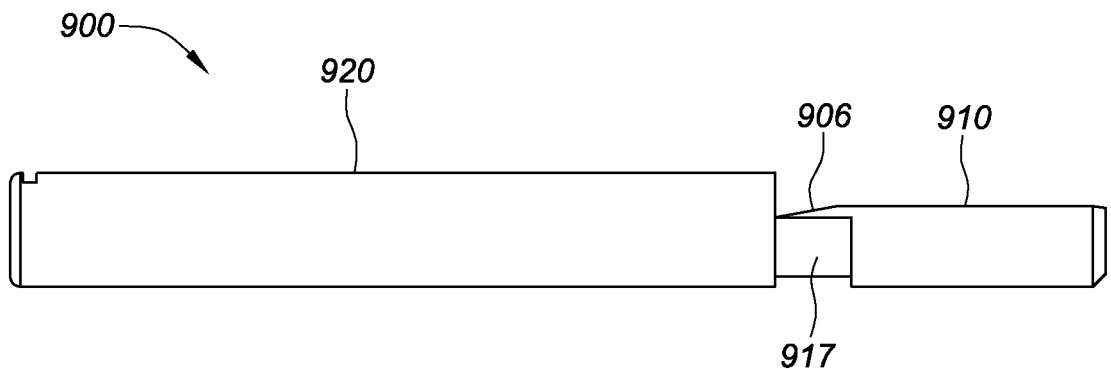
FIG. 9A is a side plan view of a coupler, consistent with various embodiments of the present disclosure.

FIG. 9A is a side plan view of a coupler 900 including a proximal portion 910 and a distal portion 920, consistent with various embodiments of the present disclosure. In the present embodiment, a pull-ring groove 917 is positioned between the proximal and distal portions, 910 and 920, respectively. The pull-ring groove 917 facilitates securing a pull-ring (part of a steering system assembly for the catheter) to the coupler 900. One or more guidewires couple to, and extend proximally from, the pull-ring. In response to tension on one or more of the guidewires, the pull-ring translates the tension on the one or more guidewires into a torque on the catheter shaft resulting in a sweep. A ramp 906 facilitates routing of a flexible circuit from an ultrasonic transducer array mounted to the distal portion 920 of the coupler 900 to the proximal portion 910.

Figure 9B:
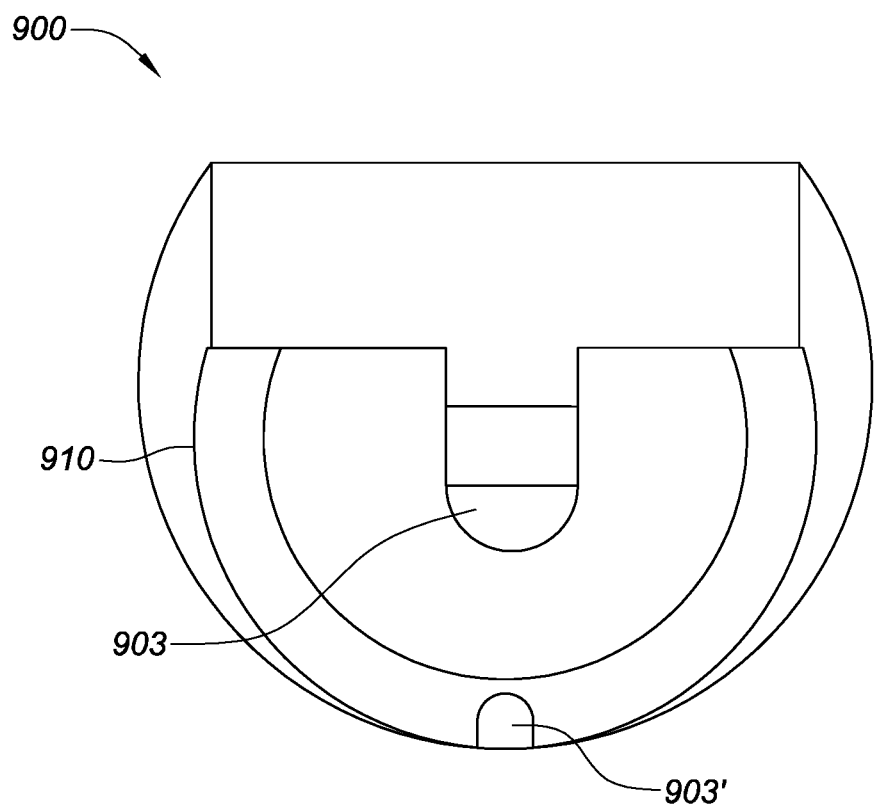
FIG. 9B is a front plan view of the coupler of FIG. 9A, consistent with various embodiments of the present disclosure.

FIG. 9B is a front plan view of the coupler 900 of FIG. 9A, consistent with various embodiments of the present disclosure. FIG. 9B shows pathways 903 and 903' for the electrical conductors and the guidewires, respectively, within a proximal portion 910 of the coupler 900.

Figure 10A:
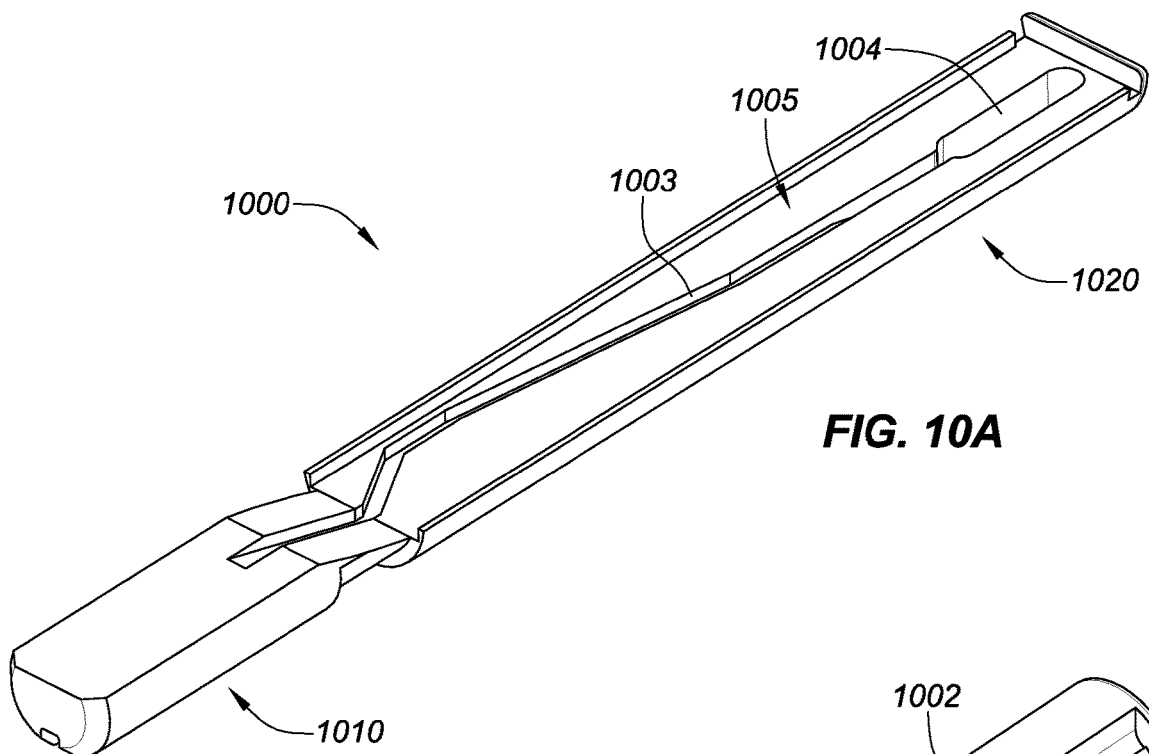
FIG. 10A is an isometric top view of a coupler for an ultrasonic transducer array catheter, consistent with various embodiments of the present disclosure.

FIG. 10A is an isometric top view of a coupler 1000 for an ultrasonic transducer array catheter, consistent with various embodiments of the present disclosure. A thermistor trench 1004 extends into a top surface 1005 of the coupler 1000, while a conductor pathway 1003 extends from the trench 1004 within a distal portion 1020 to a proximal portion 1010 of the coupler 1000. In some embodiments of the coupler 1000, the conductor pathway 1003 may veer from a collinear path with a longitudinal axis of the coupler 1000 to facilitate isolation of the electrical conductors therein from magnetic sensors placed on a back-side of the coupler. This may be particularly relevant to applications where the electrical conductors, magnetic sensors, and/or thermistor secured to the coupler 1000 are susceptible to electromagnetic interference from adjacent electronics. Positioning the magnetic sensors and thermistor on opposite sides of the coupler, and further routing the pathways for the electrical conductors away from one another may mitigate such electromagnetic interference.

Figure 10B:
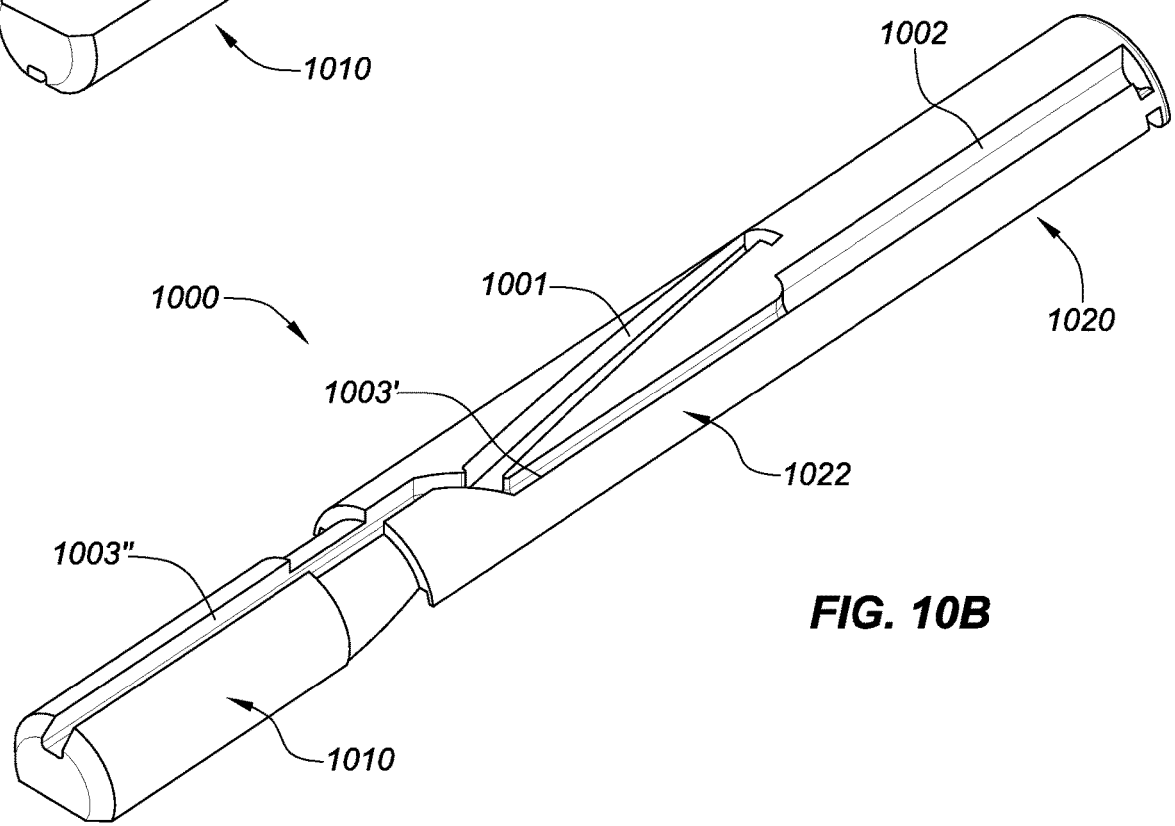
FIG. 10B is an isometric bottom view of the coupler of FIG. 10A, consistent with various embodiments of the present disclosure.

FIG. 10B is an isometric bottom view of the coupler 1000 of FIG. 10A, consistent with various embodiments of the present disclosure. As further shown in FIG. 10B, the trenches 1001 and 1002 for the magnetic sensors are longitudinally offset from one another—the first trench 1001 is located within an intermediary portion 1022 of the coupler 1000, and the second trench 1002 is placed within a distal portion 1020. The longitudinally offset relationship between the magnetic sensors may help to mitigate the likelihood of the magnetic sensors being affected by magnetic distortions (e.g., eddy currents within the magnetic field). The otherwise close proximity of the magnetic sensors in a paired configuration may result in one of the magnetic sensors creating eddy currents within the magnetic field which are detected by the other magnetic sensor.

As shown in FIG. 10B, first electrical conductors from a first magnetic sensor placed in trench 1002 may extend a length of the coupler 1000 within a dedicated pathway 1003' before merging into pathway 1003", which is shared with second electrical conductors from another magnetic sensor placed in trench 1001. Routing the first electrical conductors away from the other magnetic sensors may prevent the first electrical conductors from injecting noise on to a signal transmitted on the first electrical conductors—where the injected noise is associated with a magnetic field emanating from, or sensed by, the second magnetic sensor.

The various relative positions of the trenches for the one or more magnetic sensors and the thermistor may be dependent on the preferred assembly methodology. For example, in some embodiments, manufacturability of the assembly of FIG. 7 may be preferred for its single placement process for the magnetic sensors and thermistor. However, in some cases a two-step placement process may be preferable. In such a case, an assembly as shown in FIGS. 1A-D may be preferable. It is known that many ultrasonic transducer arrays, upon installation in a distal tip assembly, are sensitive to additional manufacturing processes; accordingly, placement of the magnetic sensors and/or thermistors prior to placement of the ultrasonic transducer array may be desirable in some applications.

U.S. provisional application No. 62/331,292, filed 3 May 2016, U.S. application Ser. No. 15/585,859, filed 3 May 2017, and international application no. PCT/US17/30828, filed 3 May 2017, are hereby incorporated by reference as though fully set forth herein.

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations. For example, while various embodiments of the present disclosure have been presented as being applicable to ultrasonic imaging catheters, the embodiments disclosed herein may be readily applied to electrophysiology and ablation catheters, as a few examples. Moreover, the catheter coupler presented herein may not be necessarily limited to intravascular/intracardiac implementations but may also find application for endoscopic catheter procedures, among others.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An intravascular catheter comprising:
an ultrasonic transducer array;
a coupler mechanically coupled to a proximal end of the ultrasonic transducer array;
a first and a second magnetic positioning sensor coupled to the coupler;
a catheter shaft coupled to a proximal end of the coupler;
a catheter handle coupled to a proximal end of the catheter shaft, the catheter handle configured and arranged to steer the catheter through a vascular lumen of a patient; and
a pull-ring directly coupled to the coupler and one or more steering wires coupled to the pull-ring, the one or more steering wires extend through a lumen of the catheter shaft to the catheter handle, the pull-ring and the one or more steering wires configured to facilitate steering the catheter via actuation of the one or more steering wires.

2. The intravascular catheter of claim 1, wherein the coupler is further configured to house and position the first and second magnetic positioning sensors at nonparallel orientations relative to one another, the two magnetic positioning sensors configured and arranged to transmit electrical signals indicative of the six degrees of freedom that the ultrasonic transducer array has within a controlled magnetic field.

3. The intravascular catheter of claim 1, wherein the ultrasonic transducer array includes a backing/insulating layer sandwiched between a plurality of ultrasonic transducers and a flexible electronic circuit, the flexible electronic circuit electrically coupled to each of the plurality of ultrasonic transducers in the array, and the insulating layer configured to absorb noise that is emitted from a back-side of the ultrasonic transducers.

4. The intravascular catheter of claim 1, further including a thermistor and electrical conductors communicatively coupled to each of the magnetic sensors; and
wherein the coupler includes a plurality of trenches extending into an outer surface of the coupler, the trenches housing the magnetic positioning sensors and the thermistor, the electrical conductors and the thermistor are routed proximally along a pathway cut into the outer surface of the coupler.

5. The intravascular catheter of claim 3, wherein the flexible electronic circuit extends over a top surface of the coupler, the backing/insulating layer and the flexible electronic circuit extend proximally into an interface feature of the coupler, the interface feature configured to mechanically support the portion of the ultrasonic transducer array that extends distally.

6. The intravascular catheter of claim 1, further including controller circuitry communicatively coupled to the first and second magnetic positioning sensors, the controller circuitry configured and arranged to determine the six degrees of freedom that the ultrasonic transducer array has within a controlled magnetic field.

7. The intravascular catheter of claim 6, wherein the controller circuitry is communicatively coupled to the ultrasonic transducer array, and further configured and arranged to create an image based on the signals received from the plurality of ultrasonic transducers.

8. The intravascular catheter of claim 1, wherein a first magnetic positioning sensor is disposed at a positive 5 degree angle, with respect to a longitudinal axis of the catheter shaft, and a second magnetic positioning sensor is disposed at a negative 5 degree angle, relative to the longitudinal axis, to create a 10 degree angular separation between the first and second magnetic position sensors.

9. The intravascular catheter of claim 1, wherein a degree of angular separation between the first and second magnetic position sensors is between 1 and 20 degrees.

10. The intravascular catheter of claim 1, wherein a degree of angular separation between the first and second magnetic position sensor is between 10 and 12 degrees.

11. The intravascular catheter of claim 6, further including a display communicatively coupled to the controller circuitry, wherein the controller circuitry is further configured and arranged to transmit data packets to the display indicative of the location of the ultrasonic transducer array within the controlled magnetic field, and the display is configured and arranged to communicate the location to a clinician.

12. A coupler assembly for an intravascular catheter comprising:
a coupler;
an ultrasonic transducer array coupled to the coupler;
first and second magnetic positioning sensors coupled to the coupler at nonparallel orientations relative to one another, the first and second magnetic positioning sensors configured and arranged to transmit an electrical signal indicative of the six degrees of freedom that the ultrasonic transducer array has within a controlled magnetic field; and
a pull-ring directly coupled to the coupler and one or more steering wires, the pull-ring and one or more steering wires configured to facilitate steering the intravascular catheter via actuation of the one or more steering wires.

13. The coupler of claim 12, wherein the ultrasonic transducer array includes a backing/insulating layer sandwiched between a plurality of ultrasonic transducers and a flexible electronic circuit, the flexible electronic circuit electrically coupled to each of the plurality of ultrasonic transducers in the array, and the insulating layer configured to absorb noise that is emitted from a back-side of the ultrasonic transducers.

14. The coupler of claim 12, the coupler further including a plurality of trenches extending into an outer surface of the coupler, the trenches housing the magnetic positioning sensors and a thermistor, electrical conductors from each of the magnetic sensors, and thermistor are routed proximally along a pathway cut into the outer surface of the coupler.

15. The coupler of claim 13, wherein the flexible electronic circuit extends over a top surface of the coupler, the backing/insulating layer and the flexible electronic circuit extend proximally into an interface feature of the coupler, the interface feature configured to mechanically support the portion of the ultrasonic transducer array that extends distally.

16. The coupler of claim 12, wherein a first magnetic positioning sensor is disposed at a positive 5 degree angle, with respect to a longitudinal axis of the catheter shaft, and a second magnetic positioning sensor is disposed at a negative 5 degree angle, relative to the longitudinal axis, to create a 10 degree angular separation between the first and second magnetic position sensors.

17. The coupler of claim 12, wherein a degree of angular separation between the first and second magnetic position sensor is between 1 and 20 degrees.

18. The coupler of claim 12, wherein a degree of angular separation between the first and second magnetic position sensor is between 10 and 12 degrees.

\* \* \* \* \*